(12) United States Patent
Bernstein

(10) Patent No.: US 8,153,687 B2
(45) Date of Patent: Apr. 10, 2012

(54) GALLIUM COMPLEXES WITH POLYALCOHOLS AND METHODS OF USE

(76) Inventor: Lawrence Richard Bernstein, Menlo Park, CA (US)

( * ) Notice: Subject to any disclaimer, the term of this patent is extended or adjusted under 35 U.S.C. 154(b) by 176 days.

(21) Appl. No.: 12/799,755

(22) Filed: Apr. 29, 2010

(65) Prior Publication Data

US 2010/0286263 A1 Nov. 11, 2010

Related U.S. Application Data

(60) Provisional application No. 61/175,585, filed on May 5, 2009.

(51) Int. Cl.
*A61K 31/28* (2006.01)
*C07F 5/00* (2006.01)

(52) U.S. Cl. ............................................ 514/492; 556/1

(58) Field of Classification Search ....... 556/1; 514/492
See application file for complete search history.

(56) References Cited

U.S. PATENT DOCUMENTS 4,822,876 A * 4/1989 Wright et al. ................. 536/121

OTHER PUBLICATIONS

Ghaschghaie et al, Dalton Transactions, vol. 39, pp. 5535-5543 (May 2010).*
Zhou et al., Journal of Applied Polymer Science, vol. 99, pp. 1620-1626 (2006).*

* cited by examiner

*Primary Examiner* — Porfirio Nazario Gonzalez

(57) ABSTRACT

Provided are complexes of gallium and polyalcohols. Also provided are pharmaceutical compositions comprising such complexes and methods of their use. Methods of preparing the complexes are also provided.

25 Claims, No Drawings

GALLIUM COMPLEXES WITH POLYALCOHOLS AND METHODS OF USE

RELATED APPLICATIONS

This application claims the benefit of U.S. provisional application 61/175,585 filed 5 May 2009.

TECHNICAL FIELD

This invention relates generally to compositions comprising gallium. More specifically, this invention relates to gallium complexes with polyalcohols.

BACKGROUND OF THE INVENTION

Gallium is used therapeutically and diagnostically in the management and treatment of cancer, infectious disease, inflammatory disease, bone disease, autoimmune disease, and other diseases and disorders. There is an ongoing need to provide gallium compositions that are well tolerated and that are therapeutically active. There is a particular need to provide such compositions that are active against infections and infection-associated biofilms. The present invention addresses these needs.

SUMMARY OF THE INVENTION

Disclosed herein are novel complexes of gallium and polyalcohols. These complexes are found to be useful for pharmaceutical applications, in particular for the treatment of infections and infection-associated biofilms.

In an embodiment of the invention, there is provided a complex of gallium and polyalcohol.

In another embodiment of the invention, there is provided a complex of a polyalcohol and gallium, wherein the molar ratio of polyalcohol to gallium is from approximately 1:1 to approximately 1:2.

In another embodiment of the invention, there is provided a complex of a polyalcohol and gallium having the formula $Ga(L)_x(OH)_2$, wherein L is a polyalcohol ligand and x is 0.5 or 1.

In another embodiment of the invention, there is provided a pharmaceutical composition comprising a pharmaceutically acceptable carrier and a pharmaceutically acceptable complex of gallium and polyalcohol.

In a further embodiment of the invention, there is provided a process for preparing a polyalcohol gallium complex that comprises reacting a gallium alkoxide in the presence of an anhydrous solvent with a polyalcohol, at a polyalcohol to gallium molar ratio of about 0.5 to about 1, to form an intermediate, then reacting the intermediate with water, at a molar ratio of water to gallium of about 1 to about 2, with the amount of polyalcohol and water being sufficient to replace all of the alkoxy groups of the gallium alkoxide, and then removing the solvent and recovering the product.

In another embodiment of the invention, there is provided a method for treating a gallium-responsive condition in a subject by administering to the subject an effective amount of a complex of gallium and polyalcohol.

DETAILED DESCRIPTION OF THE INVENTION

The following definitions are presented to assist one of ordinary skill in the art to which the invention pertains to interpret the description of the invention and the appended claim and are not meant to limit the scope of the invention and appended claims.

As used in the specification and the appended claims, the singular forms "a," "an," and "the" include plural referents unless the context clearly dictates otherwise. Thus, for example, reference to "a polyalcohol" encompasses a combination or mixture of different polyalcohol as well as a single polyalcohol.

The terms "optional" or "optionally" as used herein mean that the subsequently described circumstance may or may not occur, so that the description includes instances where the circumstance occurs and instances where it does not.

The terms "active agent," "drug," and "pharmacologically active agent" are used interchangeably herein to refer to a chemical material or compound which, when administered to an organism (human or animal, generally human) induces a desired pharmacologic effect.

The terms "to treat" and "treatment" as used herein encompass the usual meanings of these terms plus the usual meanings of the terms "to prevent" and "prevention." Thus, for example, "treatment" of a gallium responsive disease, as the term "treatment" is used herein, encompasses both prevention of a gallium responsive disease in a predisposed individual and treatment of a gallium responsive disease in an individual who has such a disease.

By the term "effective" amount of a drug is meant a sufficient amount of a compound to provide the desired effect and performance at a reasonable benefit/risk ratio as attends any medical treatment.

The term "patient" or "subject" is meant to include a human or a veterinary patient. Within the context of the present invention, veterinary patients are intended to include both mammalian and non-mammalian veterinary patients, the latter including such veterinary patients as for example, lizards and birds.

Set forth below is a description of what are currently believed to be the preferred embodiments and best examples of the claimed invention. Any alternates or modifications in function, purpose, or structure are intended to be covered by the claims of this application.

The present invention relates to complexes of gallium and polyalcohols. All such complexes are included in the invention. As used herein, the term "polyalcohol" is used in its conventional sense, referring to a chemical compound having two or more hydroxyl groups bonded to one or more carbon atoms. Polyalcohols useful in this invention include, without limitation, alkyl polyalcohols, amine polyalcohols, polyamine polyalcohols, and mixtures thereof. Particular polyalcohols useful in this invention include, without limitation, adonitol, arabitol, erythritol, propylene glycol, glycerin, galactitol, sorbitol, mannitol, ribulose, xylitol, sorbose, riboflavin, sucrose, dextrose, maltose, lactose, lactulose, ribose, mannose, galactose, fructose, diethanolamine, triethanolamine, (bis(2-hydroxyethyl)amino-2-propanol, tromethamine, 2-bis(2-hydroxyethyl)-amino-2-(hydroxymethyl)-1,3-propanediol, 1,3-bis[tris(hydroxymethyl)methyl amino]propane, and glucosamine.

Complexes of gallium and polyalcohols may be prepared in any practical way. A solution comprising such complexes may be prepared by mixing a dissolved gallium salt, such as, for example, gallium nitrate or gallium chloride, and a dissolved polyalcohol, such as, for example, xylitol, in a mutual solvent, such as, for example, water, and adjusting the pH, if necessary, to about 6 to 7.5 using a base, such as sodium carbonate. The ratio of the gallium to the polyalcohol will generally be between about 2:1 to about 1:10, preferably between about 1:1 to about 1:2. If pharmaceutically acceptable materials are used for preparing such a solution, then the solution may be pharmaceutically usable. In many cases, a complex formed will have the formula $Ga(L)_x(OH)_2$, wherein L is a polyalcohol ligand and x is 0.5 or 1, though many other useful complexes and mixtures of complexes may also form.

Gallium complexes with polyalcohols may also be prepared in the solid phase. Such complexes may have a formula of $Ga(L)_x(OH)_2$, wherein L is a polyalcohol ligand and x is 0.5 or 1, or they may have other formulas. One process for preparing such complexes in the solid phase, particularly of the formula $Ga(L)_x(OH)_2$, is reacting a gallium alkoxide in the presence of an anhydrous solvent with a polyalcohol, at a polyalcohol to gallium molar ratio of about 0.5 to about 1, to form an intermediate, then reacting the intermediate with water, at a molar ratio of water to gallium of about 1 to about 2, with the amount of polyalcohol and water being sufficient to replace all of the alkoxy groups of the gallium alkoxide, and then removing the solvent and recovering the product. The gallium alkoxide preferably has the formula $Ga(OR)_3$, where R is a carbon chain of about 1 to about 8 carbon atoms. The chain may be either straight or branched. Examples of such alkoxides are methoxide, ethoxide, isopropoxide, propoxide, butoxide, isobutoxide, amyloxide, hexoxide, octoxide, 2-ethyl-butoxide, 2-ethyl-hexoxide, and so on. A preferred alkoxide is gallium isopropoxide. This process is analogous to the process disclosed by Wright et al. (U.S. Pat. No. 4,822,876) for the synthesis of solid phase aluminum complexes with polyalcohols.

In an embodiment of the process, the gallium alkoxide is reacted in the presence of an anhydrous solvent with a polyalcohol in an amount of from about 0.5 mole to about 1 mole of polyalcohol per mole of gallium alkoxide for about 30 to about 90 minutes at about 40° C. to about 90° C. to form an intermediate, then water is added slowly in an amount of about 1 mole to about 2 moles per mole of gallium alkoxide, and the reactants heated for about 30 minutes to about 2 hours at about 40° C. to about 90° C. The reaction mixture is then cooled and the solvent removed.

The gallium complexes with polyalcohols of this invention may optionally comprise additional ligands. Any such ligand may be included; examples include citrate, nitrate, and maltolate. An example of such a mixed-ligand complex would be a complex of gallium with xylitol and citrate.

Pharmaceutical compositions comprising any of the complexes of the invention may be prepared. Such compositions will generally comprise a pharmaceutically acceptable carrier and a pharmaceutically acceptable complex of the invention. The carrier will be suited to the means of administration for which it is intended. Thus, as examples, an oral dosage form will comprise a carrier suited for oral administration and a topical dosage form will comprise a carrier suited for topical administration. The complexes of the invention may be administered by any pharmaceutically acceptable means including, without limitation, orally, topically, transdermally, rectally, buccally, vaginally, topical ocularly, intraocularly, urethrally, intralesionally, in conjunction with chemoembolization, perianally, directly into a tumor, by instillation into the bladder, into the lung as by inhalation, sublingually, intravenously, subcutaneously, intramuscularly, peritonealy, into the ear, or dentally.

The pharmaceutical compositions of the present invention may be in any acceptable state, such as for example, solid, semisolid, gel, sol, powder, and liquid compositions, as well as mixtures of any of the foregoing. Solid dosage forms include, without limitation, tablets, capsules, caplets, lozenges, troches, chewing gums, and beads. Liquid dosage forms include without limitation, liquid solutions, emulsions, suspensions, or combinations thereof. Other dosage forms contemplated under the invention include, without limitation, pastes including toothpastes, ointments, creams, aerosols, dusts, shampoos, and powders. Solid or liquid dosage forms wherein the gallium compounds are present in liposomes are also contemplated under the present invention as is animal feed that has been prepared to contain the gallium compositions of the present invention.

While the pharmaceutical compositions of the present invention may be formulated in unit dose forms, it is to be understood that they may also be formulated in divided or multiple dose forms.

The pharmaceutical compositions of the invention may comprise one or more pharmaceutically acceptable excipients appropriate to the pharmaceutical form and the intended mode of administration. Such excipients include, without limitation, pharmaceutically acceptable carriers, vehicles, propellants, disintegrants, diluents, dilutants, preservatives, pH adjusters, surface-active substances, emulsifiers, stabilizers, preservatives, coating agents, enteric coatings, buffers, absorption enhancers, solubility modifiers, flavorings, fillers, solvents, gel-forming agents, tablet excipients, antioxidants, dispersants, antifoams, flavor corrigents, solubilizers, colorants, color enhancers, dyes, pigments, permeation promoters, permeation enhancers, complexing agents, absorbents, adsorbents, acidulents, anticaking agents, sequestrants, conditioners, controlled release agents, emollients, emulsifiers, encapsulants, flow aids, fragrances, perfumes, hydrogels, hardeners, stiffeners, humectants, lubricants, moisturizers, odor masking agents, opacifiers, plasticizers solvents, spreading agents, sweeteners, UV absorbers, and viscosity modifiers.

The compositions of the invention may also be used to impregnate, coat, or otherwise treat medical and surgical equipment and devices. Such equipment and devices include, without limitation, bandages, suture material, catheters, stents, gloves, masks, prosthetic devices, implants, rods, screws, plates, valves, tubes, bags, pumps, filters, lenses, wires, cables, and so on.

Gallium-responsive diseases and disorders contemplated under the present invention include, without limitation, cancer, including breast cancer, prostate cancer, liver cancer, cancers of the bone, lymphomas, leukemias, multiple myeloma, cancers of the brain, cancers of the throat, pancreatic cancer, neck cancers, gastric cancers, intestinal cancers, colon cancers, rectal cancers, testicular cancers, bladder cancers, ovarian cancers, cervical cancers, uterine cancers, skin cancers, melanoma, ocular cancers, mouth cancers, tongue cancers, metastatic cancers, and other cancers; conditions of excessive bone resorption and/or disorders of calcium homeostasis, including osteoporosis, Paget's disease, metastatic bone disease, hyperparathyroidism, hypercalcemia, osteonecrosis, laminitis, and navicular disorders; inflammatory and/or autoimmune disorders, including rheumatoid arthritis, inflammatory arthritis, psoriasis and related dermatoses, multiple sclerosis, lupus erythematosus, Sjogren's syndrome, uveitis, asthma, Type 1 diabetes, Graves' disease, autoimmune Addison's disease, Hashimoto's thyroiditis, central nervous system vasculitis, spondylitis, inflammatory bowel disease, Crohn's disease, colitis, celiac disease, myasthenia gravis, inflammatory myopathies, scleroderma, alopecia areata, and septicemia; infectious diseases, including intracellular pathogenic diseases such as tuberculosis, Johne's disease, leprosy, listeriosis, brucellosis, typhoid fever, *Salmonella* infections, legionnaire's disease, *Rhodococcus* infections (including those caused by *Rhodococcus* equi), plague, typhus, chlamydia, leishmaniasis, trypanosomiasis, and malaria; *Pseudomonas* infections; biofilm-forming infections; biofilms; infections and biofilms associated with cystic fibrosis; Gram-positive and Gram-negative bacterial infections, including those caused by *Staphylococcus, Streptococcus, Pasteurella*, and others; neuropathies including painful peripheral neuropathies; adverse conditions of the liver, including hepatitis, hepatomegaly, and cirrhosis; splenomegaly; and other conditions that are now known, or are discovered in the future, to be responsive to gallium.

When the gallium-polyalcohol complexes are used in such a treatment method, the complexes are administered in a therapeutically effective amount to treat the gallium-responsive disease or disorder. When administered systemically, such effective amounts generally result in maximal plasma gallium concentrations of about 10 to 8,000 ng/mL, preferably about 100 to 3,000 ng/mL, and most preferably about 500 to 1,500 ng/mL.

When administered directly into a tumor or when used in chemoembolization therapy, the gallium concentrations of the injected liquid or gel are about 0.1 to about 10,000 µg/mL, preferably about 1.5 to 1,500 µg/mL, and more preferably about 100 to 1,000 µg/mL.

As an example of oral administration, a gallium xylitol complex may be administered orally at a dose of about 0.5 to 100 mg/Kg/day, preferably about 2 to 50 mg/Kg/day, and more preferably about 5 to 30 mg/Kg/day, together with a pharmaceutically acceptable carrier. The dose may be administered in a single dose once per day, or in divided doses two or more times per day.

In an embodiment of the invention wherein the gallium-polyalcohol complex is administered topically or otherwise locally, the complex is present in a pharmaceutical formulation such that the gallium content is generally about 0.00001 percent to about 10 percent by weight of the formulation, preferably about 0.005 to about 5 percent, and most preferably about 0.05 to about 1 percent.

The practice of the present invention will employ, unless otherwise indicated, conventional techniques of pharmaceutical formulation, medicinal chemistry and the like, which are within the skill of the art. Such techniques are explained fully in the literature. Preparation of various types of pharmaceutical formulations are described, for example, in REMINGTON: THE SCIENCE AND PRACTICE OF PHARMACY, 20$^{th}$ edition (Lippincott Williams & Wilkins, 2000) and Ansel et al., PHARMACEUTICAL DOSAGE FORMS AND DRUG DELIVERY SYSTEMS, 6$^{th}$ Ed. (Media, Pa.: Williams & Wilkins, 1995).

The gallium-polyalcohol complexes of the invention have additional uses outside of medicine. These uses include the control of microbial growth and/or biofilms formation on industrial equipment, including, without limitation, water processing equipment, ship and marine equipment, food processing equipment, and in any other place that is subject to adverse growth of microbes and/or biofilms.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents and publications mentioned herein are incorporated by reference in their entireties.

EXPERIMENTAL

The following examples are put forth so as to provide those of ordinary skill in the art with a complete disclosure and description of how to make and use the compositions of the invention. The examples are intended as non-limiting examples of the invention. While efforts have been made to ensure accuracy with respect to variables such as amounts, temperature, etc., experimental error and deviations should be taken into account. Unless indicated otherwise, parts are parts by weight, temperature is degrees centigrade, and pressure is at or near atmospheric. All components were obtained commercially unless otherwise indicated.

EXAMPLE 1

Preparation of an Aqueous Solution Comprising Gallium Complexed with Xylitol

To 500 mL of a 0.1 molar aqueous solution of $Ga(NO_3)_3$ is added 500 mL of a 0.2 molar aqueous solution of xylitol. The mixture is stirred with a magnetic stirring rod for five minutes. To the resulting solution, under continued stirring, solid powdered $Na_2(CO_3)$ is slowly added until the pH of the solution is 7.0. Stirring is continued for another hour. In the resulting solution, gallium complexes with xylitol.

EXAMPLE 2

Preparation of a Pharmaceutical Emulsion Containing Gallium Complexed with Xylitol An aliquot of 500 mL of the solution of Example 1 is added to 500 mL of hydrophilic petrolatum (as Aquaphor®). The mixture is stirred vigorously in a sealed rotating blade mixer to form a creamy emulsion.

EXAMPLE 3

Use of Topical Gallium-Xylitol Complex to Treat a Recalcitrant Infection by *Pseudomonas aeruginosa*

A 48-year-old man suffers from a severe diabetic foot ulcer that is infected with *Pseudomonas aeruginosa*. The infection, which involves biofilm formation, does not respond to treatments with topical triclosan, gentamicin, and ciprofloxacin, or to oral ciprofloxacin. The gallium-xylitol emulsion of Example 2 is applied to the infected area and is covered by a bandage. For the next seven days, the infected area is cleaned and the gallium-xylitol emulsion of Example 2 is then applied and covered by a bandage once per day. At the end of the seven days, the infection is clear.

EXAMPLE 4

Preparation of a Solid Phase Gallium Xylitol Complex

To a solution containing 0.5 mole of gallium isopropoxide in 500 mL of anhydrous isopropanol under nitrogen at 80° C. is added 0.5 mole of xylitol with mixing. The mixture is then maintained at 80° C. for one hour. One mole of water is then added dropwise to the solution with mixing and the mixture is maintained an additional 1.5 hours at 80° C. The reaction mixture is then cooled and the solvent is removed by distillation at reduced pressure at a temperature of about 50° C. to yield a white powder. This powder is the 1:1 complex of gallium and xylitol, with a formula of about $Ga(L)(OH)_2$, where L is the xylitol ligand.

Other 1:1 gallium complexes with polyalcohols can be prepared in a similar fashion by substituting another polyalcohol ligand for the xylitol ligand in this procedure. Similarly, the 2:1 gallium complex with a polyalcohol can be prepared by adding 0.25 mole, instead of 0.5 mole, of polyalcohol ligand to the heated anhydrous gallium isopropoxide solution in this procedure.

While certain embodiments have been described herein, it will be understood by one skilled in the art that the methods, systems, and apparatus of the present disclosure may be embodied in other specific forms without departing from the spirit thereof. The present embodiments are therefore to be considered in all respects as illustrative and not restrictive of the present disclosure. Rather, the scope and spirit of the present invention is embodied by the appended claims.

I claim:

1. A complex of a polyalcohol and gallium.
2. The complex of claim 1, wherein the polyalcohol is selected from the group consisting of alkyl polyalcohols, amine polyalcohols, polyamine polyalcohols, and mixtures thereof.
3. The complex of claim 1 wherein the polyalcohol is selected from the group consisting of adonitol, arabitol, erythritol, propylene glycol, glycerin, galactitol, sorbitol, mannitol, ribulose, xylitol, sorbose, riboflavin, sucrose, dextrose, maltose, lactose, lactulose, ribose, mannose, galactose, fructose, diethanolamine, triethanolamine, (bis(2-hydroxyethyl)amino-2-propanol, tromethamine, 2-bis(2-hydroxyethyl)-amino-2-(hydroxymethyl)-1,3-propanediol, 1,3-bis[tris(hydroxymethyl)methyl amino] propane, and glucosamine.
4. The complex of claim 1, wherein the polyalcohol is xylitol.
5. A complex of a polyalcohol and gallium, wherein the molar ratio of polyalcohol to gallium is from approximately 1:1 to approximately 1:2.
6. A complex of a polyalcohol and gallium having the formula $Ga(L)_x(OH)_2$, wherein L is a polyalcohol ligand and x is 0.5 or 1.
7. The complex of claim 6, wherein the polyalcohol is selected from the group consisting of alkyl polyalcohols, amine polyalcohols, polyamine polyalcohols, and mixtures thereof.
8. The complex of claim 6 wherein the polyalcohol is selected from the group consisting of adonitol, arabitol, erythritol, propylene glycol, glycerin, galactitol, sorbitol, mannitol, ribulose, xylitol, sorbose, riboflavin, sucrose, dextrose, maltose, lactose, lactulose, ribose, mannose, galactose, fructose, diethanolamine, triethanolamine, (bis(2-hydroxyethyl)amino-2-propanol, tromethamine, 2-bis(2-hydroxyethyl)-amino-2-(hydroxymethyl)-1,3-propanediol, 1,3-bis[tris(hydroxymethyl)methyl amino] propane, and glucosamine.
9. The complex of claim 6, wherein the polyalcohol is xylitol.
10. A pharmaceutical composition comprising a pharmaceutically acceptable carrier and the complex of claim 1.
11. The pharmaceutical composition of claim 10, wherein the composition and the carrier are suitable for oral administration.
12. The pharmaceutical composition of claim 10, wherein the composition and the carrier are suitable for topical administration.
13. The pharmaceutical composition of claim 10, wherein the composition and the carrier are suitable for rectal, buccal, transdermal, vaginal, topical ocular, intraocular, urethral, sublingual, intravenous, subcutaneous, intramuscular, peritoneal, otic, intralesional, intratumoral, inhaled, or dental administration.
14. A method for treating a gallium-responsive disease or disorder in a subject by administering to the subject an effective amount of the complex described in claim 1.
15. The method of claim 14, wherein the complex is administered by a route selected from the group consisting of rectally, buccally, transdermaly, vaginally, topical ocularly, intraocularly, urethrally, sublingually, intravenously, subcutaneously, intramuscularly, peritonealy, into the lung, into the bladder, into the ear, dentally, orally and topically.
16. The method as described in claim 14, wherein the polyalcohol is xylitol.
17. The method of claim 14 wherein the gallium-responsive disease or disorder is an infection.
18. The method as described in claim 17 wherein the infection is at least partially caused or exacerbated by *Pseudomonas aeruginosa*.
19. The method as described in claim 14 wherein a biofilm is associated with the gallium-responsive disease or disorder.
20. A method for treating a gallium-responsive disease or disorder in a subject by orally administering to said subject a dose in the range of about 0.5 to about 100 mg/Kg/day of the gallium complex of claim 1.
21. A method for treating a gallium-responsive disease or disorder in a subject by orally administering to said subject a dose in the range of about 2 to about 50 mg/Kg/day of the gallium complex of claim 1.
22. A method for treating a gallium-responsive disease or disorder in a subject by orally administering to said subject a dose in the range of about 5 to about 30 mg/Kg/day of the gallium complex of claim 1.
23. A topical formulation comprising the gallium complex as described in claim 1 wherein the gallium is present in the range of about 0.00001 percent to about 10 percent by weight of the formulation.
24. A topical formulation comprising the gallium complex as described in claim 1 wherein the gallium is present in the range of about 0.005 percent to about 5 percent by weight of the formulation.
25. A topical formulation comprising the gallium complex as described in claim 1 wherein the gallium is present in the range of about 0.05 percent to about 1 percent by weight of the formulation.

* * * * *